US006805663B1

(12) United States Patent
Bugliosi et al.

(10) Patent No.: US 6,805,663 B1
(45) Date of Patent: Oct. 19, 2004

(54) METHOD OF SHARED EROTIC EXPERIENCE AND FACILITIES FOR SAME

(76) Inventors: Vince Bugliosi, 11750 Mt. Vernon Ave., Apt. AA2006, Grand Terrace, CA (US) 92313; Liz Bugliosi, 11750 Mt. Vernon Ave., Apt. AA2006, Grand Terrace, CA (US) 92313

( * ) Notice: Subject to any disclaimer, the term of this patent is extended or adjusted under 35 U.S.C. 154(b) by 28 days.

(21) Appl. No.: 10/236,671

(22) Filed: Sep. 6, 2002

(51) Int. Cl.[7] .................................................. A61F 5/00
(52) U.S. Cl. ......................................................... 600/38
(58) Field of Search ...................... 600/28–41; 128/897, 128/898

(56) References Cited

U.S. PATENT DOCUMENTS

| | | | | |
|---|---|---|---|---|
| 3,668,810 A | * | 6/1972 | Bankston | 52/6 |
| 4,843,788 A | | 7/1989 | Gavin et al. | |
| 5,024,398 A | * | 6/1991 | Riedinger et al. | 244/118.5 |
| 5,163,447 A | | 11/1992 | Lyons | |
| 5,524,638 A | | 6/1996 | Lyons | |
| 5,651,219 A | * | 7/1997 | Baloga et al. | 52/32 |
| 5,928,170 A | | 7/1999 | Garrigan | |
| 5,980,256 A | * | 11/1999 | Carmein | 434/55 |
| 6,199,552 B1 | | 3/2001 | Crespo | |
| 6,368,268 B1 | | 4/2002 | Sandvick et al. | |

* cited by examiner

*Primary Examiner*—Samuel G. Gilbert
(74) *Attorney, Agent, or Firm*—Cislo & Thomas, LLP

(57) ABSTRACT

A method of sharing erotic experiences includes providing a building with a number of compartments, entertainment viewable from inside the compartments and surround sound music audible throughout the building, participants entering the building and go to the compartments, starting the entertainment at a proscribed time, and turning on the power from a central control booth at a proscribed time to a stimulation device for sexual pleasure found in each of the compartments. The facilities are such that sounds from the participants are transferred between the compartments, such that couples or individuals in one compartment can hear others in the building also experiencing intense sexual pleasure. The individual compartments may further contain a whirlpool tub with jets starting at a proscribed time. Importantly, security is provided to maintain order in the building, and regular cleaning and sanitizing of the compartments and stimulation device is provided.

11 Claims, 3 Drawing Sheets

METHOD OF SHARED EROTIC EXPERIENCE AND FACILITIES FOR SAME

BACKGROUND OF THE INVENTION

1. Field of the Invention

This invention relates generally to a business method for providing a shared erotic experience and to facilities to accomplish that purpose.

2. Description of the Related Art

Couples and individuals enjoy lovemaking or other expressions of sexuality typically in the privacy of their own homes. Some enjoy having sex in their homes under special conditions, such as certain stereophonic music being played, or in a semi-darkened room with only candles or a lava lamp providing mood lighting. Some like to relax in a Jacuzzi® or other brand whirlpool before or afterwards. Having a pleasant and relaxing environment for enjoying the total sexual experience is undoubtedly important.

Many couples and individuals purchase or rent adult-oriented prerecorded videocassettes or digital videodiscs, which depict other couples or individuals engaging in sex acts and are played back on television sets. In making love or masturbating while watching the same, these couples or individuals are, in a disconnected way, participating in sex with the persons on the small screen, although those persons are not physically present.

Some couples or individuals use toys or other devices to enhance their sexual experience. For example, new vibrators or clitoris stimulation devices currently available in the marketplace tend to be well designed and powerful, allowing women to experience very pleasurable and often highly vocal orgasms. The noise level of the participants can even be problematic for individuals living in an apartment with thin walls and other neighbors, particularly children, close by.

In big cities in Japan such as Tokyo, young people well into their twenties often still live at home with their parents, but need a private place to go for watching adult entertainment and having sex. Many Japanese Love Hotels have sprung up having small rooms available for a reasonable price including such entertainment, some with interesting decor including following certain themes. While not entirely different in principle than a conventional small hotel, these establishments serve their purposes in Japan.

Select couples or individuals take additional steps and attend swingers' parties or actually participate in sex with numerous others, although most feel at least somewhat uncomfortable engaging in sexual activities with strangers present. Still, for those who do attend swingers' parties or watch others engaging in sexual activities live, it is often quite arousing and enjoyable. In particular, some participants report being most aroused by the sounds of others, particularly females, having orgasms during sex or masturbation.

Certain sexual devices have long existed in the marketplace including vibrators and dildos. For example, U.S. Pat. Nos. 5,524,638 and 5,163,447 disclose amusement devices for use during sexual intercourse which emit light or sounds including music. U.S. Pat. No. 5,928,170 discloses an audio-enhanced sexual vibrator that can record and play back sounds for aural stimulation.

Additionally, it is believed through use of digital cameras and computers that certain web sites on the Internet now offer the opportunity to interact, even live, with others and engage in certain sexual practices. While this may simulate live sex and still be anonymous, nevertheless it requires imagination and is not real. Moreover, parents who have such computer equipment and software in their homes run the risk their children may access the same.

Couples and individuals on a wide scale enjoy and are comfortable with the movie going experience, including traveling to theaters, paying admission and viewing movies with the general public. Additionally, many persons enjoy films or light shows displayed on large screens much bigger than could fit inside their homes. IMAX® theaters in California and elsewhere provide reclining seats and display films on the ceiling of geodesic domes. Griffith Park Observatory in Los Angeles has such facilities and similarly puts on laser light shows with surround sound music that many persons find relaxing and enjoyable. Although such might be nice environments in which to have sex, sexual activity in public places is viewed as lewd behavior and generally unlawful.

SUMMARY OF THE INVENTION

A method of sharing erotic experiences includes providing a building with a number of compartments and entertainment viewable from inside the compartments. Participants enter the building and the compartments and the entertainment starts at a prescribed time. Preferably shortly thereafter, a stimulation device for sexual pleasure starts in each of the compartments. Then the facilities are such that sounds from the participants are transmitted between the compartments, such that couples or individuals in one compartment can hear couples or individuals in other compartments.

For the method of the present invention to be a viable business, admission may to be charged for entering the building, for use of the compartments and for the entertainment. The entertainment is preferably a light show or a film in conjunction with surround-sound music. The individual compartments may further contain a whirlpool tub the jets of which start at a prescribed time. Importantly, security is provided to maintain order in the building. Also importantly, regular sanitizing of the stimulation device and cleaning of the compartments are provided.

Facilities for the shared erotic experience preferably include a building with a specially configured high ceiling and means for displaying the light show or film thereon. The individual compartments are preferably open at the top but have a lockable door. In each of the compartments there is an area for reclining, preferably a large chaise lounge. The stimulation devices are preferably in communication with a central power source such that they can be turned on at the prescribed times. The stimulation device or portions thereof are preferably easily detachable for regular cleaning purposes.

The building may include a ticket booth to sell admission into the building and compartments, and a central control booth to control starting the entertainment, stimulation devices and whirlpool tubs prescribed times. Transmitting and receiving of the sounds may be accomplished or enhanced by microphones and speakers in each of the compartments. Color monitors may be provided inside each compartment upon which the entertainment is displayed.

OBJECTS OF THE INVENTION

It is an object of the present invention to provide a way and a place for adult couples and individuals to have sexual relations under as many of the above-identified desirable conditions as possible.

It is a further object of the invention to provide a method for adult couples and individuals to share real erotic experiences with other members of the general public without physical contact.

It is a further object of the invention to provide adult members of the general public with facilities for such real erotic experiences.

It is a further object of the invention to provide a way and facilities for adult couples and individuals to hear the sounds of other adult couples or individuals experiencing intense sexual pleasure without face-to-face contact.

It is a further object of the invention to provide other entertainment in conjunction with the shared erotic experience.

It is a further object of the invention to provide a complete set of facilities for an ultimate sexual experience for adult couples and individuals.

It is a further object of the invention to provide the shared erotic experience in a safe and secure manner.

It is a further object of the present invention to provide the shared erotic experience in sanitary and spotless facilities.

It is a further object of the invention to conduct the shared erotic experience according to a specific timeline to enhance the experience.

Other objects of the present invention will become apparent from the detailed description, which follows.

DESCRIPTION OF THE PREFERRED EMBODIMENT(S)

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
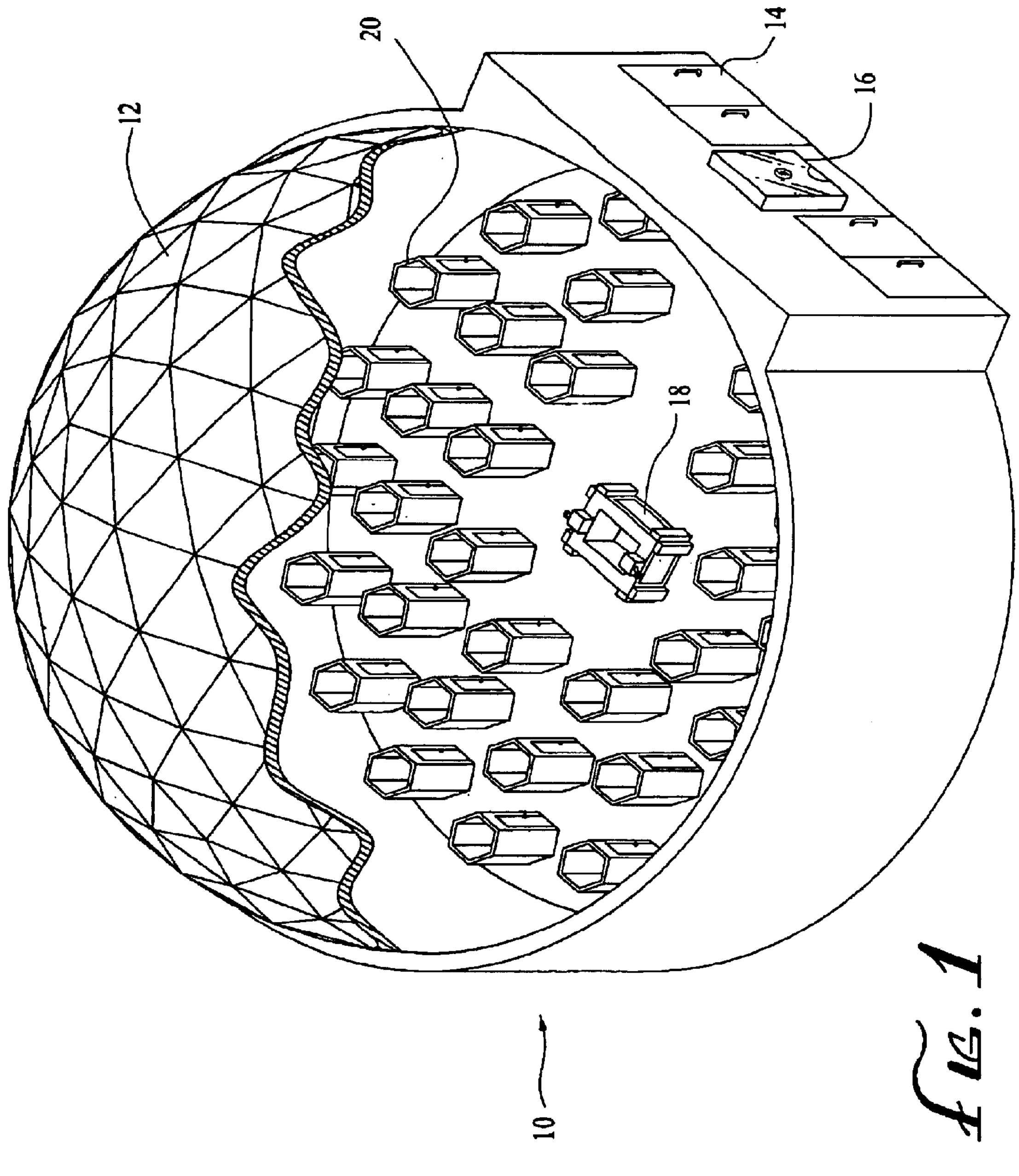
FIG. 1 is a perspective view of the overall facilities of the present invention, with a portion of the roof removed only for purposes of illustration.

Referring first to FIG. 1, shown is a large building 10 with a geodesic truss structure, domed roof 12 with a portion removed only for purposes of illustrating the contents. On the exterior of the building 10 are a plurality of doors 14 and a ticket booth 16. Inside the building 10 is a control booth and concessions stand 18, and a plurality of compartments 20. The compartments 20 are separated such that they have no common walls 22. The building 10 is carpeted on the inside.

Figure 2:
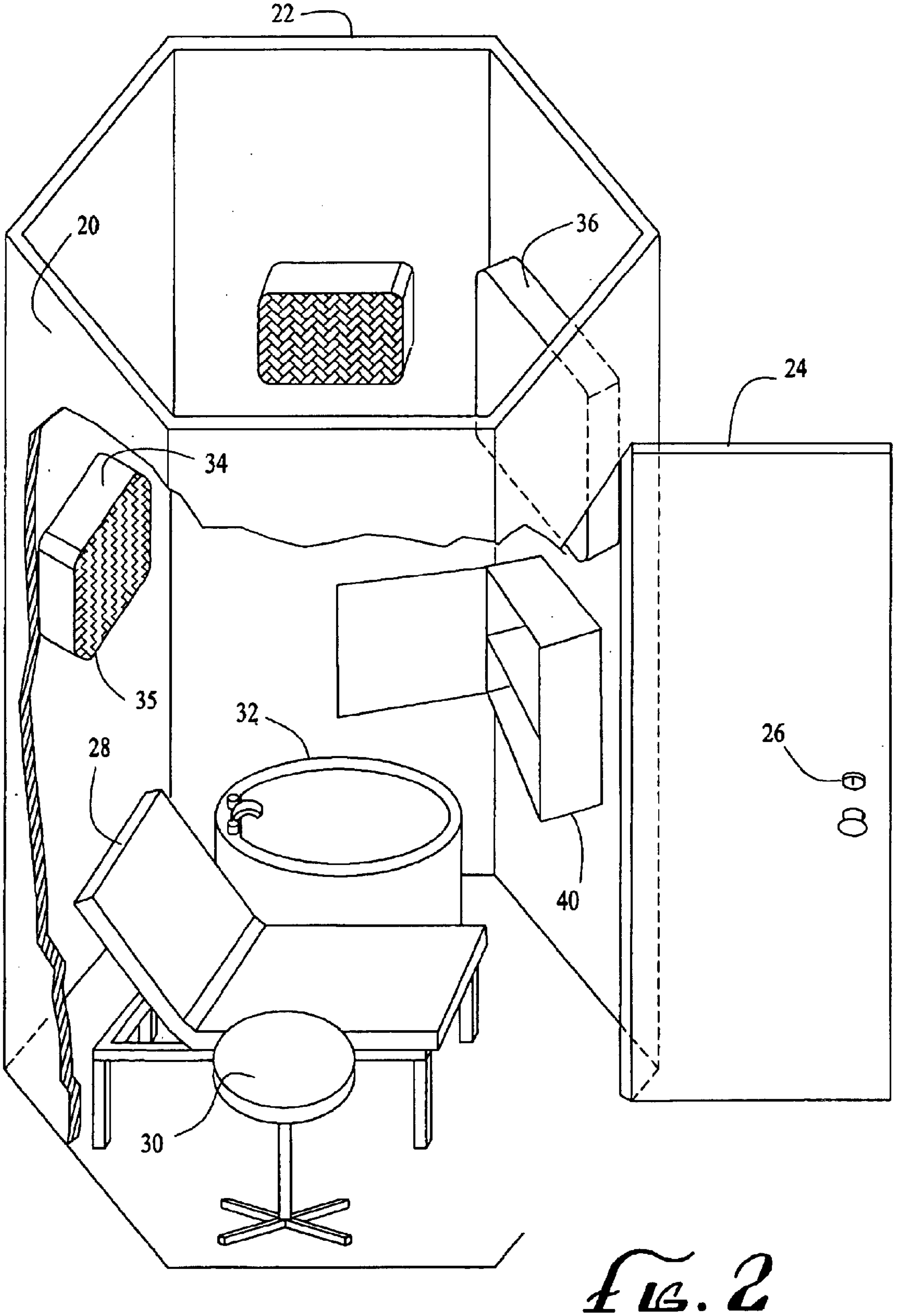
FIG. 2 is an overall perspective view of the individual compartments of the present invention, with a portion of the compartment wall removed only for purposes of illustration.

Next referring to FIG. 2, shown is a typical compartment 20 having six (6) side walls 22 about eight (8) feet high with a portion of the walls 22 removed only for purposes of illustrating the contents. The compartment 20 further includes a door 24 having a lock 26. Inside the compartment 20 is a large chaise lounge 28 of suitable size for two (2) persons to recline, and the large chaise lounge is covered with a plastic or cloth form-fitted sheet. Optionally, there may be another chair or stool 30 in each compartment 20. Also inside the compartment is a Jacuzzi® or other popular brand whirlpool bathing tub 32, again large enough for two (2) persons. Attached to the inside wall 22 of the compartment 20 is optionally a pair of speakers 34 each with a volume control 35, and a television monitor 36. Further attached to the inside wall 22 is a cabinet 40 with a door that swings out and several shelves.

Figure 3:
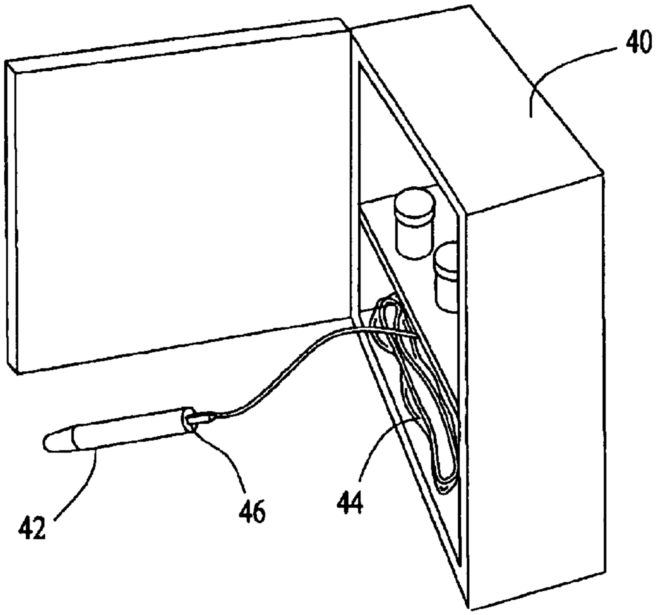
FIG. 3 is an overall perspective view of a cabinet and the stimulation device of the present invention.

Now referring to FIG. 3, shown is the cabinet 40 and its contents including a clitoris stimulation device or electrically-powered vibrator 42, and a power cord 44 approximately ten (10) feet in length. Preferably the power cord 44 is such that it is plugged in elsewhere in the compartment 20 near the chaise lounge 28, so the cord 44 need not extend across the compartment 20 and become a hazard the participants might trip over. The inventors recommend a mini-bullet clitoris stimulator like the one distributed by P.C.I. of North Hollywood, Calif. The rear portion of stimulation device 42 is detachable from the power cord 44, and may include a built in microphone 46. Alternatively, the microphone 46 may be located elsewhere in the compartment 20. Other creams and lotions might also be provided in the cabinet 40.

Figure 4:
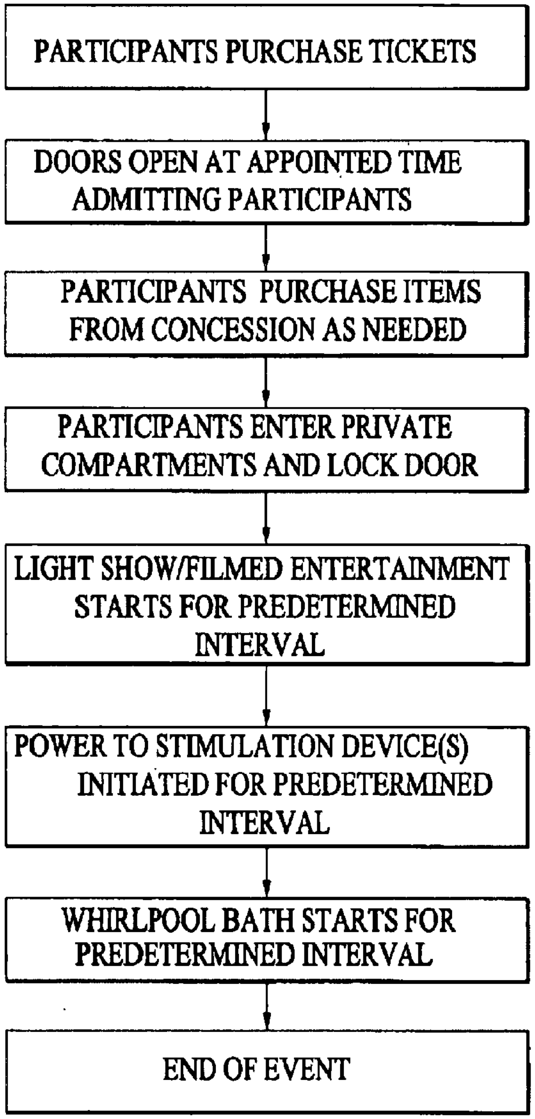
FIG. 4 is a flowchart showing the timeline of the method of the present invention.

Also referring to FIG. 4, operation and use of the facilities is now described. Participants purchase tickets at the ticket booth 16 and at the appointed time are admitted to the building 10 through the doors 14. Upon entry participants may purchase various items from the concessions stand 18, including refreshments or perhaps condoms. Then the participants enter their assigned compartment 20 and close and lock the door 24. Once inside it is anticipated the participants will at least partially disrobe and relax on the chaise lounge 28. Shortly thereafter management personnel in the control booth 18 will start the entertainment, which may consist of a laser light show or other films displayed on the dome ceiling 12 inside the building 10, which should be visible to the participants through the opening in the top of each of the compartments 20. Additionally, the show may also be displayed on the optional television monitor 36 inside each compartment 20. Stereophonic sound or music may also be broadcast at a low volume level throughout the building 10.

Next the personnel in the control booth 18 will turn on the power to the sexual stimulation device 42 located in the cabinet 40. At this time the participants can remove the stimulation device 42 from the cabinet and pull it over to the chaise lounge 28, for use as they see fit. It is anticipated through use of the stimulation device 42, that many of the participants will express sexual pleasure through loud noises, which will travel through the opening in the top of the compartments 20. These sounds then will be heard by other participants in other compartments 20 in the building 10. If necessary, through the microphone 46 in the stimulation device 42 the sounds of the participants may be transmitted and amplified to speakers 34 found in the compartments 20 of others.

At some point in time the personnel at the control booth 18 will also turn on the jets in the Jacuzzi® or other brand whirlpool bath tub 32. This will give the participants an opportunity to relax in the tub 32 perhaps, perhaps after use of the stimulation device 42. Importantly, during the show security personnel will patrol the inside of the building 10 to maintain order and prevent disorderly conduct.

Then the event will come to an end, and the participants will get dressed, and exit the compartments 20 and building 10. Afterwards, sanitation personnel will thoroughly clean each of the compartments 20 and change the sheet on the chaise lounge 28. Importantly, sanitation personnel will remove from the power cord 44 and replace the used stimulation device 42 with one that has been sterilized and is encased in a disposable plastic sleeve.

What is claimed is:

1. A method of sharing erotic experiences comprising the steps of:

providing a building with a plurality of compartments and entertainment viewable from inside the compartments;

admitting participants to the building and the compartments;

starting the entertainment viewable from inside the compartments at a prescribed time;

starting a stimulation device for sexual pleasure in each of the compartments at a prescribed time; and, transferring sounds from the participants between the compartments.

2. The method of sharing erotic experiences of claim 1 further comprising the step of charging admission into the building for use of the compartments and for the entertainment.

3. The method of sharing erotic experiences of claim 1 wherein the entertainment is a light or film show, in conjunction with surround-sound music.

4. The method of sharing erotic experiences of claim 1 further comprising the step of starting a hot water tub in each of the compartments at a prescribed time.

5. The method of sharing erotic experiences of claim 1 further comprising the step of providing security to maintain order in the building.

6. The method of sharing erotic experiences of claim 1 further comprising the step of providing regular sanitation to maintain cleanliness inside the compartments.

7. Facilities for a shared erotic experience comprising:

a building with a high ceiling and having a plurality of walled compartments each without a ceiling; and, a hot water tub for each compartment, the compartments containing furniture for reclining thereon and a stimulation device for sexual pleasure, whereby sounds may be easily transferred between the compartments for entertainment of participants.

a building with a high ceiling and having a plurality of walled compartments each without a ceiling; and, the compartments containing furniture for reclining thereon and a stimulation device for sexual pleasure, whereby sounds may be easily transferred between the compartments for entertainment of participants, and wherein the stimulation devices are coupled to a central control booth.

8. The facilities for a shared erotic experience of claim 7 wherein the stimulation device is detachable from the power cord for cleaning purposes after each use.

9. The facilities for a shared erotic experience of claim 7 further comprising means for displaying visual entertainment on the ceiling of the building and providing music audible at a low volume throughout the building.

10. The facilities for a shared erotic experience of claim 7 wherein the ceiling of the building is specially configured for displaying entertainment viewable from all of the compartments.

11. Facilities for a shared erotic experience comprising:

a building with a high ceiling and having a plurality of walled compartments each without a ceiling; and, the compartments containing furniture for reclining thereon and a stimulation device for sexual pleasure, whereby sounds may be easily transferred between the compartments for entertainment of participants, and wherein the stimulation devices are coupled to a central control booth.

* * * * *